(12) United States Patent
Wildgoose

(10) Patent No.: US 10,497,551 B2
(45) Date of Patent: Dec. 3, 2019

(54) STORAGE RING FOR FAST PROCESSES

(71) Applicant: Micromass UK Limited, Wilmslow (GB)

(72) Inventor: Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/107,534

(22) PCT Filed: Dec. 18, 2014

(86) PCT No.: PCT/GB2014/053746
§ 371 (c)(1),
(2) Date: Jun. 23, 2016

(87) PCT Pub. No.: WO2015/097444
PCT Pub. Date: Jul. 2, 2015

(65) Prior Publication Data
US 2016/0329200 A1 Nov. 10, 2016

(30) Foreign Application Priority Data

Dec. 24, 2013 (EP) ..................................... 13199548
Dec. 24, 2013 (GB) .................................... 1322981.0

(51) Int. Cl.
*H01J 49/00* (2006.01)
*H01J 49/06* (2006.01)
*G01N 27/62* (2006.01)

(52) U.S. Cl.
CPC .......... *H01J 49/062* (2013.01); *G01N 27/622* (2013.01); *H01J 49/0031* (2013.01)

(58) Field of Classification Search
CPC .. H01J 49/00; H01J 49/02; H01J 49/06; H01J 49/061; H01J 49/062; H01J 49/063;
(Continued)

(56) References Cited

U.S. PATENT DOCUMENTS 5,905,258 A 5/1999 Clemmer et al.
6,744,043 B2 6/2004 Laboda
(Continued)

FOREIGN PATENT DOCUMENTS

GB 2441198 5/2011
GB 2493602 4/2016

*Primary Examiner* — Jason L McCormack
(74) *Attorney, Agent, or Firm* — Womble Bond Dickinson (US) LLP; Deborah M. Vernon; Heath T. Misley

(57) ABSTRACT

An ion storage device is provided which is arranged and adapted: (i) to receive first ions which have been temporally separated according to a first physico-chemical property during a first cycle of operation; (ii) to store the first ions in a first plurality of separate sections of the ion storage device so that first ions having different first physico-chemical properties are stored in different sections of the ion storage device; (iii) to receive second ions which have been temporally separated according to the first physico-chemical property during a second subsequent cycle of operation; and (iv) to store the second ions in the ion storage device so that the first and second ions are simultaneously stored within the ion storage device and so that at least some of the first and second ions having substantially the same first physico-chemical property are stored in the same section of the ion storage device.

19 Claims, 1 Drawing Sheet

(58) Field of Classification Search
CPC ........ H01J 49/065; H01J 49/40; H01J 49/403;
H01J 49/4205; H01J 49/421; H01J
49/4215; H01J 49/422; H01J 49/426
USPC .......................... 250/281, 282, 283, 287, 291
See application file for complete search history.

(56) References Cited

U.S. PATENT DOCUMENTS

| | | | |
|---|---|---|---|
| 8,629,409 B2 | 1/2014 | Kovtoun | |
| 9,111,654 B2 | 8/2015 | Giles et al. | |
| 9,147,563 B2 | 9/2015 | Makarov | |
| 9,343,285 B2 | 5/2016 | Green et al. | |
| 2008/0048113 A1* | 2/2008 | Franzen | H01J 49/4225 250/292 |
| 2009/0014641 A1* | 1/2009 | Bateman | H01J 49/062 250/282 |
| 2009/0078866 A1* | 3/2009 | Li | H01J 49/425 250/297 |
| 2009/0314935 A1* | 12/2009 | Hoyes | H01J 49/4235 250/283 |
| 2013/0105681 A1 | 5/2013 | Kovtoun | |

* cited by examiner

STORAGE RING FOR FAST PROCESSES

CROSS REFERENCE TO RELATED APPLICATIONS

This application is the National Stage of International Application No. PCT/GB2014/053746, filed 18 Dec. 2014 which claims priority from and the benefit of United Kingdom patent application No. 1322981.0 filed on 24 Dec. 2013 and European patent application No. 13199548.2 filed on 24 Dec. 2013. The entire content of these applications are incorporated herein by reference.

BACKGROUND TO THE PRESENT INVENTION

The present invention relates to an ion storage device, a mass spectrometer, a method of storing ions and a method of mass spectrometry. The preferred embodiment relates to an ion storage device coupled between an ion mobility spectrometer or separator which operates over a first cycle time (e.g. 10 ms) and a second device such as a quadrupole mass filter or mass analyser which operates over a second slower cycle time (e.g. 100 ms).

It is known to couple an ion mobility spectrometer which typically operates over a cycle time of e.g. 10 ms to a Time of Flight mass analyser which typically operates over a faster cycle time of e.g. 100 µs. The ability to couple an ion mobility spectrometer to a faster Time of Flight mass analyser is due to the inherently fast analysis time offered by Time of Flight mass spectrometers which can, for example, acquire a complete mass spectrum very quickly e.g. in a timescale of 100 µs.

As a result, nested ion mobility spectrometry-Time of Flight acquisitions can be performed without loss of performance of either the ion mobility spectrometer or the Time of Flight mass spectrometer.

The coupling of an ion mobility spectrometer to a Time of Flight mass analyser has proven to be a powerful technique.

However, it is problematic to attempt to couple an ion mobility spectrometer or separator to other devices which operate on much slower time scales than Time of Flight mass spectrometers and ion mobility spectrometers or separators. For example, Fourier Transform mass spectrometers such as FT-ICR and electrostatic mass spectrometers, mass filters such as quadrupoles, ion traps and fragmentation devices such as Electron Transfer Dissociation ("ETD") fragmentation devices, Electron Capture Dissociation ("ECD") fragmentation devices and Proton Transfer Reaction ("PTR") devices are comparatively slow and operate over a longer cycle time than conventional ion mobility spectrometers.

As an example, Electron Transfer Dissociation fragmentation devices, Electron Capture Dissociation fragmentation device and Proton Transfer Reaction devices typically operate over a timescale >100 ms and hence the separation of ions by an ion mobility separator over a timescale of 10 ms is too fast for such devices.

It will be apparent, therefore, that it is problematic to attempt to couple an ion mobility spectrometer or separator to certain other devices such as Fourier Transform mass spectrometers, quadrupoles, ion traps and fragmentation devices.

GB-2441198 (Franzen) discloses an ion storage bank comprising an array of RF multipoles arranged in parallel.

It is desired to provide an improved mass spectrometer and method of mass spectrometry.

SUMMARY OF THE PRESENT INVENTION

According to an aspect of the present invention there is provided an ion storage device arranged and adapted:

(i) to receive first ions which have been temporally separated according to a first physico-chemical property during a first cycle of operation;

(ii) to store said first ions in a first plurality of separate sections of said ion storage device so that first ions having different first physico-chemical properties are stored in different sections of said ion storage device;

(iii) to receive second ions which have been temporally separated according to said first physico-chemical property during a second subsequent cycle of operation; and (iv) to store said second ions in said ion storage device so that said first and second ions are simultaneously stored within said ion storage device and so that at least some of said first and second ions having substantially the same first physico-chemical property are stored in the same section of said ion storage device.

The present invention is concerned with improving the coupling of fast separation or analytical devices such as ion mobility spectrometers or separators to comparatively slower separation or analytical devices such as Fourier Transform mass analysers, quadrupole mass filters or mass analysers, ion traps and fragmentation devices.

The preferred embodiment relates to an ion storage device which preferably comprises a storage ring or ring ion guide which is arranged to store ions emerging from a comparatively fast device such as an ion mobility spectrometer or separator and then after one or more cycles of operation of the ion mobility spectrometer or separator have been performed the ion storage device is arranged to onwardly transmit the ions to a comparatively slower device such as a Fourier Transform mass spectrometer.

The preferred embodiment provides the capability to couple fast separation techniques such as ion mobility separation to slower analytical devices such as mass filters, certain types of mass analysers, ion traps and fragmentation devices.

According to a preferred embodiment the ion storage device comprises a travelling wave closed loop ion guide which is preferably arranged downstream of a fast separation device such as an ion mobility spectrometer or separator.

The preferred embodiment operates by synchronising the cyclic period of the ion storage device with the separation time of the fast separation device (e.g. ion mobility spectrometer or separator).

GB-2441198 (Franzen) does not disclose storing ions from multiple separations so that the ions are simultaneously stored within an ion storage device so that ions from different separations having substantially the same first physico-chemical property are stored in the same section of the ion storage device.

Paragraph 52 of GB-2441198 (Franzen) discloses an arrangement wherein a storage bank stores the ions from 30 separation runs in 30 fillable storage cells. Accordingly, ions from multiple different separations having the same physico-chemical property are not stored in the same section of the ion storage device.

A person skilled in the art will recognise that there a number of problems associated with the arrangement disclosed in GB-2441198 (Franzen). In particular, as is apparent from FIG. 4A ions are only stored in every third storage cell. As a result, the storage cell contemplated in GB-2441198 (Franzen) would be physically large and would have complicated electronics requirements as is evident from FIG. 3.

Furthermore, the arrangement disclosed in GB-2441198 (Franzen) suffers from a complex mechanism in relation to transferring ions between storage cells. As is apparent from FIG. 3C of GB-2441198 (Franzen) and the related description, a DC voltage is superimposed upon a pseudo-potential. This can give rise to undesired mass to charge ratio separation of ions as ions are being transferred between storage cells.

The ion storage device according to the present invention advantageously does not suffer from the problems experienced by the arrangement disclosed in GB-2441198 (Franzen). In particular, the ion storage device according to the present invention can be made small and compact as it can store ions in adjacent storage regions in contrast to the arrangement disclosed in GB-2441198 (Franzen) which can only store ions in every third storage cell.

Furthermore, advantageously the ion storage device according to the present invention does not suffer from mass to charge ratio separation effects when transferring ions between storage regions.

The application of a plurality of transient DC voltages to the plurality of electrodes forming the ion storage device according to the present invention is particularly advantageous as it represents a less complex, more compact and distortion free method of translating ions around the ion storage device.

The present invention is therefore particularly advantageous compared to the arrangement disclosed in GB-2441198 (Franzen).

The ion storage device is preferably arranged and adapted to store the second ions in the ion storage device so that at least some of the first and second ions having substantially the same first physico-chemical property are stored in the same section of the ion storage device.

According to an alternative less preferred embodiment the ion storage device may be arranged and adapted to store the second ions in the ion storage device so that at least some of the first and second ions having substantially the same first physico-chemical property are stored in different, adjacent or intermediate sections of the ion storage device.

The ion storage device preferably further comprises a plurality of electrodes.

The plurality of electrodes preferably comprise a plurality of electrodes each having one or more electrodes through which ions are transmitted.

The plurality of electrodes may comprise a plurality of segmented rod electrodes. The plurality of segmented rod electrodes preferably comprises a plurality of segmented quadrupole rod electrodes, a plurality of segmented hexapole rod electrodes, a plurality of segmented octapole rod electrodes or a segmented multipole arrangement comprising more than eight rod electrodes.

The ion storage device preferably further comprises a device arranged and adapted to apply an RF voltage to the plurality of electrodes in order to confine ions radially within the ion storage device.

The ion storage device preferably further comprises a device arranged and adapted to apply one or more transient DC voltages to the plurality of electrodes in order to urge or cause ions to be translated along the length of the ion storage device.

The ion storage device preferably comprises a closed loop ion guide.

The ion storage device is preferably arranged and adapted to cause ions to undergo one or more circuits or loops of the closed loop ion guide before being ejected from the ion storage device.

The ion storage device is preferably arranged and adapted to cause ions to undergo one or more circuits or loops of the closed loop ion guide without causing the ions to reverse direction or direction of rotation.

The ion storage device is preferably arranged and adapted to cause ions to undergo one or more circuits or loops of the closed loop ion guide wherein ions are caused to reverse direction or direction of rotation one or more times.

The ion storage device is preferably arranged and adapted to be maintained in a mode of operation at a pressure selected from the group consisting of: (i) <0.0001 mbar; (ii) 0.0001-0.001 mbar; (iii) 0.001-0.01 mbar; (iv) 0.01-0.1 mbar; (v) 0.1-1.0 mbar; (vi) 1-10 mbar; (vii) 10-100 mbar; (viii) 100-1000 mbar; and (ix) >1000 mbar.

The ion storage device is preferably arranged and adapted to store at least some or substantially all ions within the ion storage device either: (i) in order of the first physico-chemical property or another property; (ii) in reverse order of the first physico-chemical property or another property; (iii) in a mixed order of the first physico-chemical property or another property; or (iv) in a random, pseudo-random or substantially random order.

The ion storage device is preferably arranged and adapted to eject at least some or substantially all ions within the ion storage device either: (i) in order of the first physico-chemical property or another property; (ii) in reverse order of the first physico-chemical property or another property; (iii) in a mixed order of the first physico-chemical property or another property; or (iv) in a random, pseudo-random or substantially random order.

The ion storage device is preferably arranged and adapted to onwardly eject or read out substantially all ions stored within the ion storage device from the ion storage device preferably over a period of time.

The ion storage device may be arranged and adapted to onwardly eject or read out only some sub-groups of ions stored within the ion storage device. According to an embodiment the ion storage device may be arranged and adapted to cause other sub-groups of ions which are initially stored within the ion storage device to be substantially attenuated within the ion storage device so that the other sub-groups of ions are not onwardly ejected or read out from the ion storage device.

According to another aspect of the present invention there is provided a mass spectrometer comprising an ion storage device as described above.

The mass spectrometer preferably further comprises a first device arranged upstream and/or downstream of the ion storage device, wherein the first device is arranged and adapted to cause ions to become temporally separated according to the first physico-chemical property.

The first physico-chemical property preferably comprises ion mobility, collision cross section, interaction cross section or differential ion mobility.

The first device preferably comprises an ion mobility separator or a differential ion mobility separator.

The first physico-chemical property may alternatively comprise mass or mass to charge ratio.

The first device may alternatively comprise a time of flight region, an ion trap or a mass analyser.

The first device is preferably arranged and adapted to perform multiple cycles of operation wherein ions are temporally separated according to the first physico-chemical during each cycle of operation and wherein each cycle of operation has a first time period T1.

The ion storage device is preferably arranged and adapted to rotate and/or translate ions along and/or around the ion storage device with a second rotational time period T2.

The ion storage device is preferably arranged and adapted to rotate ions around the ion storage device with a second rotational time period T2 that substantially matches the first time period T1. According to less preferred embodiments the second rotational time period T2 may be a fraction or an integer multiple of the first time period T1.

The ion storage device is preferably arranged and adapted to rotate ions around the ion storage device with a rotational period T2 wherein T2/T1 is selected from the group consisting of: (i) <0.1; (ii) 0.1-0.2; (iii) 0.2-0.3; (iv) 0.3-0.4; (v) 0.4-0.5; (vi) 0.5-0.6; (vii) 0.6-0.7; (viii) 0.7-0.8; (ix) 0.8-0.9; (x) 0.9-1; (xi) 1-2; (xii) 2-3; (xiii) 3-4; (xiv) 4-5; (xv) 5-6; (xvi) 6-7; (xvii) 7-8; (xviii) 8-9; (xix) 9-10; and (xx) >10.

The mass spectrometer preferably further comprises a second device which is arranged and adapted to receive ions ejected from the ion storage device.

The second device is preferably arranged and adapted to perform multiple cycles of operation wherein ions are processed, fragmented, reacted, mass filtered, mass analysed or detected during each cycle of operation and wherein each the cycle of operation has a third time period T3.

According to the preferred embodiment T3>T1 and/or T3>T2.

The second device preferably comprises a mass analyser.

The mass analyser preferably comprises a quadrupole mass analyser or an ion trap mass analyser.

The mass analyser preferably comprises a Fourier Transform mass analyser or an electrostatic mass analyser.

The mass analyser is preferably arranged and adapted to generate an electrostatic field having a quadro-logarithmic potential distribution.

The mass analyser is preferably arranged and adapted to detect image current from ions confined by one or more electrostatic fields.

The mass analyser is preferably arranged and adapted to convert the detected image current using a Fourier transformation into frequency data and/or mass spectral data.

The second device preferably comprises a reaction, collision or fragmentation device.

According to an embodiment ions ejected from the ion storage device are passed to the first device.

Ions ejected from the ion storage device are preferably passed to the first device and are caused to become temporally separated according to the first physico-chemical property or a different physico-chemical property. For example, according to an embodiment ions may initially be separated according to their ion mobility in the first device before being stored in the ion storage device. When the ions are released from the ion storage device they may be passed back to the first device which may then be operated in a different mode of operation so as to separate ions according to their mass or mass to charge ratio rather than their ion mobility. The ion mobility spectrometer may be switched between modes by varying the speed at which transient DC voltages are applied to the electrodes forming the ion mobility spectrometer wherein the transient DC voltages urge ions along the length of the ion mobility spectrometer.

According to another aspect of the present invention there is provided a method of storing ions comprising:

receiving first ions which have been temporally separated according to a first physico-chemical property during a first cycle of operation;

storing the first ions in a first plurality of separate sections of an ion storage device so that first ions having different first physico-chemical properties are stored in different sections of the ion storage device;

receiving second ions which have been temporally separated according to the first physico-chemical property during a second subsequent cycle of operation; and storing the second ions in the ion storage device so that the first and second ions are simultaneously stored within the ion storage device and so that at least some of the first and second ions having substantially the same first physico-chemical property are stored in the same section of the ion storage device.

According to an aspect of the present invention there is provided a mass spectrometer comprising:

an ion mobility spectrometer arranged and adapted to perform multiple cycles of operation wherein during each cycle of operation ions are separated temporally according to their ion mobility; and a closed loop ion guide arranged and adapted to receive ions which have been temporally separated by the ion mobility spectrometer wherein ions eluting from multiple cycles of operation of the ion mobility spectrometer are simultaneously stored within the closed loop ion guide.

According to an aspect of the present invention there is provided a method of mass spectrometry comprising:

performing multiple cycles of operation of an ion mobility spectrometer wherein during each cycle of operation ions are separated temporally according to their ion mobility; and receiving ions which have been temporally separated by the ion mobility spectrometer within a closed loop ion guide wherein ions eluting from multiple cycles of operation of the ion mobility spectrometer are simultaneously stored within the closed loop ion guide.

According to another aspect of the present invention there is provided an ion storage device comprising a plurality of electrodes, wherein the ion storage device is arranged and adapted:

(i) to receive first ions which have been temporally separated according to a first physico-chemical property during a first cycle of operation;

(ii) to store the first ions in a first plurality of separate sections of the ion storage device so that first ions having different first physico-chemical properties are stored in different sections of the ion storage device;

(iii) to receive second ions which have been temporally separated according to the first physico-chemical property during a second subsequent cycle of operation;

(iv) to store the second ions in the ion storage device so that the first and second ions are simultaneously stored within the ion storage device and so that at least some of the first and second ions having substantially the same first physico-chemical property are stored in the same section of the ion storage device; and (v) to apply one or more transient DC voltages to the plurality of electrodes in order to urge or cause ions to be translated along the length of the ion storage device.

According to another aspect of the present invention there is provided a method of storing ions comprising:

receiving first ions which have been temporally separated according to a first physico-chemical property during a first cycle of operation;

storing the first ions in a first plurality of separate sections of an ion storage device comprising a plurality of electrodes so that first ions having different first physico-chemical properties are stored in different sections of the ion storage device;

receiving second ions which have been temporally separated according to the first physico-chemical property during a second subsequent cycle of operation;

storing the second ions in the ion storage device so that the first and second ions are simultaneously stored within the ion storage device and so that at least some of the first and second ions having substantially the same first physico-chemical property are stored in the same section of the ion storage device; and applying one or more transient DC voltages to the plurality of electrodes in order to urge or cause ions to be translated along the length of the ion storage device.

According to an aspect of the present invention there is provided an ion storage device arranged and adapted:

(i) to receive first ions which have been temporally separated according to a first physico-chemical property during a first cycle of operation;

(ii) to store the first ions in a first plurality of separate sections of the ion storage device so that first ions having different first physico-chemical properties are stored in different sections of the ion storage device;

(iii) to receive second ions which have been temporally separated according to the first physico-chemical property during a second subsequent cycle of operation; and (iv) to store the second ions in the ion storage device so that the first and second ions are simultaneously stored within the ion storage device.

According to an aspect of the present invention there is provided a method of storing ions comprising:

receiving first ions which have been temporally separated according to a first physico-chemical property during a first cycle of operation;

storing the first ions in a first plurality of separate sections of an ion storage device so that first ions having different first physico-chemical properties are stored in different sections of the ion storage device;

receiving second ions which have been temporally separated according to the first physico-chemical property during a second subsequent cycle of operation; and storing the second ions in the ion storage device so that the first and second ions are simultaneously stored within the ion storage device.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv)

dibenzothiophene; (xvi) 1,10'-phenanthroline; (xvii) 9'-anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

A preferred embodiment of the present invention will now be described with reference to FIG. 1.

Figure 1:
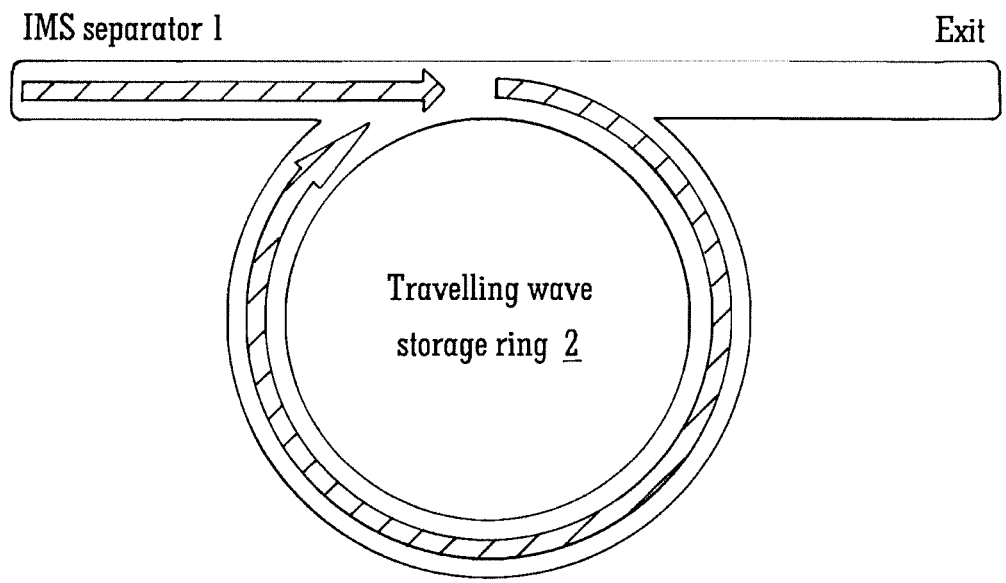
FIG. 1 shows a preferred embodiment wherein a travelling wave ion storage ring is arranged downstream of an ion mobility spectrometer or separator and is arranged in a mode of operation to receive ions eluting from the ion mobility spectrometer or separator such that the ions subsequently make one or more circuits around the ion storage ring.

FIG. 1 shows a preferred embodiment of the present invention wherein an ion mobility spectrometer or separator 1 is provided upstream of an ion storage device 2. The ion storage device 2 preferably comprises an ion guide 2.

The ion mobility spectrometer or separator 1 is preferably arranged to separate ions temporally according to their ion mobility. The ion storage device 2 preferably comprises a travelling wave ion guide wherein one or more transient DC voltages are applied to electrodes which form the ion storage device 2. The electrodes preferably comprise a plurality of electrodes having one or more apertures through which ions are transmitted in use. However, less preferred embodiments are contemplated wherein the electrodes comprise axially segmented rod electrodes. For example, according to an embodiment a segmented quadrupole, hexapole, octapole or multipole arrangement comprising more than eight rods may be provided. As will be understood by those skilled in the art, RF voltages are preferably applied to the electrodes in order to cause ions to be radially confined within the ion guide by confining ions radially within a pseudo-potential barrier.

According to the preferred embodiment the one or more transient DC voltages are preferably applied to the electrodes comprising the ion storage device 2 in order to urge or otherwise cause ions to be translated along the length of the ion storage device or ion guide 2. The transient DC voltages may be applied to the electrodes in order to cause ions to translate along or move or rotate around the entire length of the ion storage device 2.

However, according to other embodiments transient DC voltages may only be applied to certain sections of the ion storage device 2. It is contemplated that a substantially constant DC voltage may be applied to certain portions of the ion storage device 2 in order to urge ions along one or more sections of the ion storage device 2.

Ions are preferably confined radially within the ion storage device 2 by applying RF voltages to the electrodes comprising the ion storage device or ion guide 2 in order to cause ions to be confined radially by generating a pseudo-potential barrier which acts to confine ions radially within the ion storage device 2.

The ion storage device or ion guide 2 is preferably arranged to operate at elevated pressures so that ions are preferably confined radially within the ion storage device or the ion guide 2 at a relatively high pressure. For example, the ion storage device 2 may be arranged to be operated or otherwise maintained at a pressure $>10^{-3}$ mbar.

Ions preferably elute from the ion mobility spectrometer or separator 1 and are preferably sampled by the travelling wave ion storage device or ion guide 2. The ion storage device or ion guide 2 is preferably arranged so as to form a ring or other shaped ion guide wherein ions may undertake one or more orbits of the ring ion guide prior to being ejected from the ion storage device or ion guide 2.

According to a preferred embodiment ions are preferably caused to be translated or otherwise rotated around at least a portion or substantially the whole length of the ion storage device or ion guide 2. The rotational period that ions are caused to be translated or rotated around the travelling wave ion storage device or ion guide 2 is preferably arranged so that the rotational period substantially matches an operational cycle time of the ion mobility spectrometer or separator 1. According to the preferred embodiment the rotational period for ions to undertake one orbit of the ion storage device or ion guide 2 preferably matches an ion mobility separation cycle time or the time between successive pulses of ions into the ion mobility spectrometer or separator 1.

For example, according to an embodiment ions may be pulsed into the ion mobility spectrometer or separator 1 once every 10 ms and ions may be caused to separate temporally according to their ion mobility over a corresponding timescale of up to 10 ms. In such embodiments ions received within the ion storage device or ion guide 2 are then preferably caused to rotate or orbit around the ion storage device or ion guide 2 over a corresponding timescale of 10 ms.

According to a less preferred embodiment ions may be caused to rotate or orbit around the ion storage device 2 over a timescale which is an integer multiple of the cycle time of the ion mobility spectrometer 1 e.g. the rotational period may be 20 ms, 30 ms, 40 ms etc. According to another less preferred embodiment ions may be caused to rotate or orbit around the ion storage device 2 over a timescale which is a fraction of the cycle time of the ion mobility spectrometer 1 e.g. 2 ms, 4 ms, 6 ms etc.

The approach as described above of substantially matching or coupling the rotational movement of ions around the ion storage device or ion guide 2 with the cycle time of an ion mobility spectrometer or separator (or other separation device) 1 preferably allows multiple ion mobility spectrometer cycles to be completed and sampled such that the same ion mobility drift time regions from multiple different ion mobility spectrometer cycles are preferably stored within the same sections of the ion storage device or ion guide 2. For example, according to an embodiment ions may be confined axially within the ion storage device or ion guide 2 within a plurality of different axial potential wells. The axial potential wells are preferably created by applying one or more transient DC voltages to the electrodes forming the ion storage device or ion guide 2. Ions having substantially the same ion mobility (or other physico-chemical property) from multiple ion mobility separations are preferably stored within the same sections of the ion storage device 2.

The fidelity of the storage process is a function of the number of travelling waves or the number of axial potential barriers present in the ion storage device or ion guide 2 which in turn is dependent upon the spacing of the travelling waves and the length of the ion storage device or ion guide 2.

Figure 2:
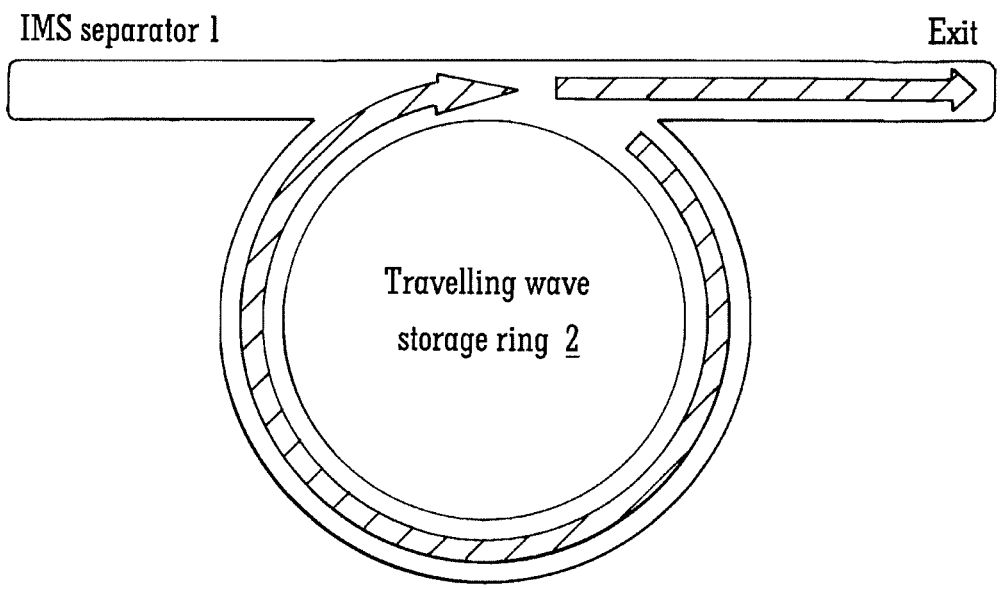
FIG. 2 shows a preferred embodiment of the present invention wherein in a mode of operation ions stored within the ion storage ring pass to an exit of the ion storage ring and are then onwardly transmitted to a downstream ion-optical device which preferably comprises a device such as a quadrupole, ion trap, Fourier Transform mass analyser or fragmentation device which operates over a longer cycle time than the ion mobility spectrometer or separator.

FIG. 2 shows how ions which have been confined within the ion storage device or ion guide 2 are preferably ejected from the ion storage device or ion guide 2 to e.g. a downstream mass analyser, preferably a Fourier Transform mass analyser. The time taken to eject the ions from the ion storage device or ion guide 2 is preferably chosen based on the characteristics of the downstream analyser. For example, the ejection time may differ when coupling the ion storage device or ion guide 2 to a Fourier Transform mass spectrometer wherein the read out time may be of the order of seconds or when coupling the ion storage device or ion guide 2 to a quadrupole mass filter or mass analyser wherein the read out time may be of the order of 100 ms or longer.

According to a less preferred embodiment the velocity of the travelling wave or the speed at which transient DC voltages are preferably applied to the electrodes forming the ion storage device 2 may be chosen such that multiple ion mobility separations are arranged to be captured and to follow each other within the ion storage device or ion guide 2. According to an embodiment the rotational or cycle time of the ion storage device 2 may be twice the cycle time of the ion mobility spectrometer or separator 1. For example, ions eluting from the ion mobility spectrometer or separator 1 from a first cycle of operation may be confined within a first half of the ion storage device 2. Ions eluting from the ion mobility spectrometer or separator 1 from a second subsequent cycle of operation may be confined within a second half of the ion storage device 2. Ions eluting from the ion mobility spectrometer or separator 1 from a third subsequent cycle of operation may be confined within the first half of the ion storage device 2 and ions eluting from the ion mobility spectrometer or separator 1 from a fourth subsequent cycle of operation may be confined within the second half of the ion storage device 2. As a result, the first half of the ion storage device 2 may comprise ions from the first, third, fifth etc. cycles of operation of the ion mobility spectrometer or separator 1 and the second half of the ion storage device 2 may comprise ions from the second, fourth, sixth etc. cycles of operation of the ion mobility spectrometer or separator 1.

In the event that the ion mobility spectrometer or separator 1 has a cycle time of 10 ms and the second device has a cycle time of 100 ms, then ions from up to ten separate separations in the ion mobility spectrometer or separator 1 may be simultaneously stored in the ion storage device 2 before the ions are then released to the second device.

During the read out stage the order in which various ion species stored within the ion storage device or ion guide 2 are read out need not necessarily be the same order in which the ions initially eluted from the ion mobility spectrometer or separator 1 and were trapped within different sections, trapping regions or axial potential wells formed within the ion storage device 2.

The ion storage device or ion guide 2 may act as a filter wherein only a restricted range of ions are stored per cycle and/or wherein some but not all of the ions received from the ion mobility spectrometer or separator 1 are ejected onwardly either to a downstream ion-optical device such as a Fourier Transform mass analyser, ion trap, quadrupole mass filter or mass analyser or a fragmentation device or according to another embodiment are ejected back to the ion mobility spectrometer or separator 1.

The storage ring geometry which is preferably utilised according to the preferred embodiment may be based upon multipole devices including quadrupoles, hexapoles, octopoles and stacked ring ion guides. The ion storage device 2 may comprise a RF and DC confined ion guide such as is disclosed in WO2012/120297 (the subject-matter of which is incorporated herein by reference) according to an embodiment of the present invention.

According to an embodiment filtering techniques may be implemented within the ion storage device 2 e.g. undesired ions may be mass selectively ejected from the ion storage device 2, for example, by applying a supplemental AC voltage to at least some of the electrodes forming the ion storage device 2 in order to cause undesired ions to be ejected radially from the ion storage device 2.

According to further embodiments of the present invention fast separations other than ion mobility separation may also benefit from the approach as described above. In particular, the ion storage device 2 according to the preferred embodiment may be arranged downstream of a device other than an ion mobility spectrometer or separator i.e. it is contemplated that the first device may comprise a device which separates ions temporally according to a physico-chemical property other than ion mobility (e.g. mass or mass to charge ratio, differential ion mobility etc.)

Although the use of travelling waves or transient DC voltages applied to the electrodes forming the ion storage device 2 is particularly preferred, other embodiments are contemplated wherein axial and/or tangential electric fields may be utilised to drive ions around the whole or at least a portion of the ion storage device 2.

The angle(s) of entrance of ions into the ion storage device 2 and the angle(s) of exit of ions from the ion storage device 2 may be different. According to an embodiment the entrance(s) and/or exit(s) into and from the ion storage device 2 may be provided at different positions to those shown in FIGS. 1-2 and in particular the entrance angle and/or the exit angle need not be tangential.

Although the ion storage device 2 preferably comprises a circular ion storage ring other embodiments are contemplated wherein the ion storage device 2 does not comprise a totally circular ion guide. For example, according to an embodiment the ion storage device 2 may include sharp angles including right angle turns and have an ion path which is substantially rectangular or polygonal in shape rather than circular.

The ion storage device 2 may have multiple entry and/or exit points rather than a single entry and exit point as shown and described above with reference to FIGS. 1-2. The entry and exit points can be at the same point or at different points.

According to an embodiment ions which have been ejected from the ion storage device 2 may be arranged to pass back through the ion mobility spectrometer or separator 1 in a reverse direction to the direction that the ions initially passed through the ion mobility spectrometer or separator 1 prior to being received within the ion storage device 2.

Embodiments are contemplated wherein multiple ion storage devices 2 may be combined or provided either in series or in parallel and ions may be routed or switched between multiple ion storage devices 2 which may be provided in a chain.

The travelling wave velocity (speed) of one or more transient DC voltages or potentials which are preferably applied to the electrodes forming the ion storage device 2 or the ion storage ring 2 may vary within the cycle time. For example, according to an embodiment the travelling wave velocity may periodically be reduced to zero for a period of time.

The storage ring cycle time may be arranged to reflect the range of drift times of the ion mobility spectrometer eluents as opposed to the ion mobility spectrometer cycle time.

According to an embodiment multidimensional storage rings or cylinders may be utilised.

Although the present invention has been described with reference to preferred embodiments, it will be understood by those skilled in the art that various changes in form and detail may be made without departing from the scope of the invention as set forth in the accompanying claims.

The invention claimed is:

1. An ion storage device comprising a traveling wave closed loop ion guide comprising a plurality of electrodes, wherein said plurality of electrodes comprise a plurality of electrodes each having one or more apertures through which ions are transmitted, in use, as the ions orbit the ion storage device or wherein said plurality of electrodes comprise a plurality of axially segmented rod electrodes, arranged and adapted:
  (i) to receive from a first device upstream of said ion storage device first ions which have been temporally separated according to a first physico-chemical property during a first cycle of operation of the first device;
  (ii) to store said first ions in a first plurality of separate sections of said ion storage device so that first ions having different first physico-chemical properties are stored in different sections of said ion storage device;
  (iii) to receive from the first device second ions which have been temporally separated according to said first physico-chemical property during a second subsequent cycle of operation of the first device; and
  (iv) to store said second ions in said ion storage device so that said first and second ions are simultaneously stored within said ion storage device and so that at least some of said first and second ions having substantially the same first physico-chemical property are stored in the same section of said ion storage device;
  wherein said ion storage device further comprises a device arranged and adapted to apply one or more transient DC voltages to said plurality of electrodes having one or more apertures or to said plurality of axially segmented rod electrodes in order to create plural travelling waves that urge or cause ions to be translated along the length of said closed loop ion guide, thereby rotating ions around the ion storage device;
  wherein said first device is arranged and adapted to perform multiple cycles of operation wherein ions are temporally separated according to said first physico-chemical property during each cycle of operation and wherein each cycle of operation has a time period equal to a first time period T1, and wherein said ion storage device is arranged and adapted to rotate and/or translate ions along and/or around said ion storage device with a rotational time period T2, wherein the rotational time period T2 substantially matches said first time period T1.

2. An ion storage device as claimed in claim 1, wherein said plurality of axially segmented rod electrodes comprises a plurality of axially segmented quadrupole rod electrodes, a plurality of axially segmented hexapole rod electrodes, a plurality of axially segmented octapole rod electrodes or an axially segmented multipole arrangement comprising more than eight rod electrodes.

3. An ion storage device as claimed in claim 1, further comprising a device arranged and adapted to apply an RF voltage to said plurality of electrodes in order to confine ions radially within said ion storage device.

4. An ion storage device as claimed in claim 1, wherein said ion storage device is arranged and adapted to perform at least one of:
  cause ions to undergo one or more circuits or loops of said closed loop ion guide before being ejected from said ion storage device;
  cause ions to undergo one or more circuits or loops of said closed loop ion guide without causing said ions to reverse direction or direction of rotation; and
  cause ions to undergo one or more circuits or loops of said closed loop ion guide wherein ions are caused to reverse direction or direction of rotation one or more times.

5. An ion storage device as claimed in claim 1, wherein said ion storage device is arranged and adapted to be maintained in a mode of operation at a pressure selected from the group consisting of: (i) <0.0001 mbar; (ii) 0.0001-0.001 mbar; (iii) 0.001-0.01 mbar; (iv) 0.01-0.1 mbar; (v) 0.1-1.0 mbar; (vi) 1-10 mbar; (vii) 10-100 mbar; (viii) 100-1000 mbar; and (ix) >1000 mbar.

6. An ion storage device as claimed in claim 1, wherein said ion storage device is arranged and adapted to perform at least one of:
  store at least some or substantially all ions within said ion storage device either: (i) in order of said first physico-chemical property or another property; (ii) in reverse order of said first physico-chemical property or another property; (iii) in a mixed order of said first physico-chemical property or another property; or (iv) in a random, pseudo-random or substantially random order; and
  eject at least some or substantially all ions within said ion storage device either: (i) in order of said first physico-chemical property or another property; (ii) in reverse order of said first physico-chemical property or another property; (iii) in a mixed order of said first physico-chemical property or another property; or (iv) in a random, pseudo-random or substantially random order.

7. An ion storage device as claimed in claim 1, wherein said ion storage device is arranged and adapted to either:
  onwardly eject or read out substantially all ions stored within said ion storage device from said ion storage device preferably over a period of time; or
  onwardly eject or read out only some sub-groups of ions stored within said ion storage device, optionally wherein said ion storage device is arranged and adapted to cause other sub-groups of ions which are initially stored within said ion storage device to be substantially attenuated within said ion storage device so that said other sub-groups of ions are not onwardly ejected or read out from said ion storage device.

8. A mass spectrometer comprising an ion storage device as claimed in claim 1, said mass spectrometer optionally further comprising a first device arranged upstream and/or downstream of said ion storage device, wherein said first device is arranged and adapted to cause ions to become temporally separated according to said first physico-chemical property.

9. A mass spectrometer as claimed in claim 8, wherein said first physico-chemical property comprises ion mobility, collision cross section, interaction cross section or differential ion mobility; wherein said first device comprises an ion mobility separator or a differential ion mobility separator.

10. A mass spectrometer as claimed in claim 8, wherein said first physico-chemical property comprises mass or mass to charge ratio; wherein said first device comprises a time of flight region, an ion trap or a mass analyser.

11. A mass spectrometer as claimed in claim 8, further comprising a second device which is arranged and adapted to receive ions ejected from said ion storage device; optionally wherein said second device is arranged and adapted to perform multiple cycles of operation wherein ions are processed, fragmented, reacted, mass filtered, mass analysed or detected during each cycle of operation and wherein each said cycle of operation has a third time period T3; optionally wherein T3>T1 and/or T3>T2.

12. A mass spectrometer as claimed in claim 11, wherein said second device comprises a mass analyser.

13. A mass spectrometer as claimed in claim 12, wherein said mass analyser comprises a quadrupole mass analyser or an ion trap mass analyser.

14. A mass spectrometer as claimed in claim 12, wherein said mass analyser comprises a Fourier Transform mass analyser or an electrostatic mass analyser; wherein said mass analyser is arranged and adapted to generate an electrostatic field having a quadro-logarithmic potential distribution; wherein said mass analyser is arranged and adapted to detect image current from ions confined by one or more electrostatic fields; wherein said mass analyser is arranged and adapted to convert said detected image current using a Fourier transformation into frequency data and/or mass spectral data.

15. A mass spectrometer as claimed in claim 11, wherein said second device comprises a reaction, collision or fragmentation device.

16. A mass spectrometer as claimed in claim 8, wherein ions ejected from said ion storage device are passed to said first device; wherein ions ejected from said ion storage device are passed to said first device and are caused to become temporally separated according to said first physico-chemical property or a different physico-chemical property.

17. A method of storing ions comprising:
receiving, from a first device upstream of said ion storage device, first ions which have been temporally separated according to a first physico-chemical property during a first cycle of operation of the first device;
storing said first ions in a first plurality of separate sections of an ion storage device so that first ions having different first physico-chemical properties are stored in different sections of said ion storage device;
receiving, from the first device, second ions which have been temporally separated according to said first physico-chemical property during a second subsequent cycle of operation of the first device; and
storing said second ions in said ion storage device so that said first and second ions are simultaneously stored within said ion storage device and so that at least some of said first and second ions having substantially the same first physico-chemical property are stored in the same section of said ion storage device;
wherein said ion storage device comprises a travelling wave closed loop ion guide comprising a plurality of electrodes, wherein said plurality of electrodes comprise a plurality of electrodes each having one or more apertures through which ions are transmitted, in use, as the ions orbit the ion storage device or wherein said plurality of electrodes comprise a plurality of axially segmented rod electrodes;
wherein the method comprises applying one or more transient DC voltages to said plurality of electrodes in order to create plural travelling waves that urge or cause ions to be translated along the length of said closed loop ion guide, thereby rotating ions around the ion storage device;
wherein said first device performs multiple cycles of operation wherein ions are temporally separated according to said first physico-chemical during each cycle of operation and wherein each cycle of operation has a time period equal to a first time period T1, and wherein said ion storage device rotates and/or translates ions along and/or around said ion storage device with a rotational time period T2, wherein the rotational time period T2 substantially matches said first time period T1.

18. A mass spectrometer comprising:
an ion mobility spectrometer arranged and adapted to perform multiple cycles of operation wherein during each cycle of operation ions are separated temporally according to their ion mobility, wherein each cycle of operation has a time period equal to a first time period T1; and
an ion storage device comprising a travelling wave closed loop ion guide arranged and adapted to receive ions which have been temporally separated by said ion mobility spectrometer wherein ions eluting from multiple cycles of operation of said ion mobility spectrometer are simultaneously stored within said closed loop ion guide;
wherein said closed loop ion guide comprises a plurality of electrodes, wherein said plurality of electrodes comprise a plurality of electrodes each having one or more apertures through which ions are transmitted, in use, as the ions orbit the ion storage device or wherein said plurality of electrodes comprise a plurality of axially segmented rod electrodes;
wherein said ion storage device further comprises a device arranged and adapted to apply one or more transient DC voltages to said plurality of electrodes in order to create plural travelling waves that urge or cause ions to be translated along the length of said closed loop ion guide, thereby rotating ions around the ion storage device;
wherein said ion storage device is arranged and adapted to rotate and/or translate ions along and/or around said ion storage device with a rotational time period T2, wherein the rotational time period T2 substantially matches said first time period T1.

19. A method of mass spectrometry comprising:
performing multiple cycles of operation of an ion mobility spectrometer wherein during each cycle of operation ions are separated temporally according to their ion mobility, wherein each cycle of operation has a time period equal to a first time period T1; and
receiving ions which have been temporally separated by said ion mobility spectrometer within an ion storage device comprising a travelling wave closed loop ion guide wherein ions eluting from multiple cycles of operation of said ion mobility spectrometer are simultaneously stored within said closed loop ion guide;
wherein said closed loop ion guide comprises a plurality of electrodes, wherein said plurality of electrodes comprise a plurality of electrodes each having one or more apertures through which ions are transmitted, in use, as the ions orbit the ion storage device or wherein said plurality of electrodes comprise a plurality of axially segmented rod electrodes;

wherein the method comprises applying one or more transient DC voltages to said plurality of electrodes in order to create plural travelling waves that urge or cause ions to be translated along the length of said closed loop ion guide, thereby rotating ions around the ion storage device;

wherein said ion storage device rotates and/or translates ions along and/or around said ion storage device with a rotational time period T2, wherein the rotational time period T2 substantially matches said first time period T1.

\* \* \* \* \*